United States Patent
Jacky et al.

(10) Patent No.: US 10,301,668 B2
(45) Date of Patent: May 28, 2019

(54) COMPETITIVE PROBES FOR ENGINEERING SIGNAL GENERATION

(71) Applicant: ChromaCode, Inc., Carlsbad, CA (US)

(72) Inventors: Lucien A. E. Jacky, Orange, CA (US); Aditya Rajagopal, Orange, CA (US); Karen L. Menge, San Marcos, CA (US); Gregory Gosch, San Diego, CA (US)

(73) Assignee: CHROMACODE, INC., Carlsbad, CA (US)

( * ) Notice: Subject to any disclaimer, the term of this patent is extended or adjusted under 35 U.S.C. 154(b) by 0 days.

(21) Appl. No.: 15/677,772

(22) Filed: Aug. 15, 2017

(65) Prior Publication Data

US 2018/0057864 A1    Mar. 1, 2018

Related U.S. Application Data

(63) Continuation of application No. PCT/US2017/024933, filed on Mar. 30, 2017.

(60) Provisional application No. 62/317,151, filed on Apr. 1, 2016.

(51) Int. Cl.
| | |
|---|---|
| *C12P 19/34* | (2006.01) |
| *C12Q 1/6818* | (2018.01) |
| *C12Q 1/6804* | (2018.01) |
| *C12Q 1/6827* | (2018.01) |
| *C12Q 1/6888* | (2018.01) |
| *G01N 21/64* | (2006.01) |
| *G01N 33/58* | (2006.01) |
| *C12Q 1/6816* | (2018.01) |
| *C12Q 1/686* | (2018.01) |

(52) U.S. Cl.
CPC ......... *C12Q 1/6818* (2013.01); *C12Q 1/6804* (2013.01); *C12Q 1/686* (2013.01); *C12Q 1/6816* (2013.01); *C12Q 1/6827* (2013.01); *C12Q 1/6888* (2013.01); *G01N 21/6428* (2013.01); *G01N 33/58* (2013.01); *C12Q 2537/143* (2013.01)

(58) Field of Classification Search
USPC .......... 435/6.1, 6.11, 6.12, 91.1, 91.2, 91.51, 435/183; 436/94, 501; 536/23.1, 24.3, 536/24.33, 25.3
See application file for complete search history.

(56) References Cited

U.S. PATENT DOCUMENTS

| | | | |
|---|---|---|---|
| 5,538,848 | A | 7/1996 | Livak et al. |
| 5,882,856 | A | 3/1999 | Shuber |
| 5,928,862 | A | 7/1999 | Morrison |
| 7,348,141 | B2 | 3/2008 | French et al. |
| 7,473,767 | B2 | 1/2009 | Dimitrov |
| 7,919,237 | B2 | 4/2011 | Dimitrov et al. |
| 8,148,512 | B2 | 4/2012 | Dimitrov et al. |
| 8,492,094 | B2 | 7/2013 | Dimitrov et al. |
| 8,838,394 | B2 | 9/2014 | Kartalov et al. |
| 8,877,464 | B2 | 11/2014 | Babiel et al. |
| 9,260,761 | B2 | 2/2016 | Tyagi et al. |
| 9,366,632 | B2 | 6/2016 | Link et al. |
| 9,441,266 | B2 | 9/2016 | Larson et al. |
| 2002/0146734 | A1 | 10/2002 | Ortyn et al. |
| 2009/0042735 | A1 | 2/2009 | Blair et al. |
| 2010/0233686 | A1 | 9/2010 | Higuchi et al. |
| 2011/0151459 | A1 | 6/2011 | Rothmann et al. |
| 2011/0207623 | A1 | 8/2011 | Dimitrov et al. |
| 2012/0040349 | A1 | 2/2012 | Von Lode et al. |
| 2012/0045756 | A1 | 2/2012 | Rothmann et al. |
| 2012/0196283 | A1 | 8/2012 | Babiel et al. |
| 2013/0040841 | A1 | 2/2013 | Saxonov et al. |
| 2014/0171341 | A1 | 6/2014 | Jouvenot et al. |
| 2014/0213471 | A1 | 7/2014 | Rajagopal et al. |
| 2015/0057178 | A1 | 2/2015 | Kartalov et al. |
| 2015/0275295 | A1 | 10/2015 | Wang et al. |

FOREIGN PATENT DOCUMENTS

| | | |
|---|---|---|
| WO | WO-2006079049 A2 | 7/2006 |
| WO | WO-2013116780 A1 | 8/2013 |
| WO | WO-2017173035 A1 | 10/2017 |

OTHER PUBLICATIONS

Holland, et al., Detection of specific polymerase chain reaction product by utilizing the 5' to 3' exonuclease activity of Thermus aquaticus DNA polymerase. PNAS (USA) 88:7276-7280, 1991.
International search report and written report dated Jun. 22, 2017 for PCT Application No. PCT/US2017/24933.
Co-pending U.S. Appl. No. 15/914,356, filed Mar. 7, 2018.
Gandelman, et al., Novel Bioluminescent Quantitative Detection of Nucleic Acid Amplification in Real-Time, PLoS One, 2010, 5(11):e14155, 14 pages.
Han et al., Quantum-dot-tagged microbeads for multiplexed optical coding of biomolecules. Nature Biotechnology, 19(7):631-635, 2001.

(Continued)

*Primary Examiner* — Frank W Lu
(74) *Attorney, Agent, or Firm* — Wilson Sonsini Goodrich & Rosati

(57) ABSTRACT

A method of identifying a first target nucleic acid comprising, providing a sample comprising the first target nucleic acid, providing a first set of paired oligonucleotides with complementarity to the first target nucleic acid, the first set of paired oligonucleotides comprising a first ratio of (a) first competitive oligonucleotides to (b) first signal oligonucleotides comprising a signal tag, wherein the competitive oligonucleotides compete with the signal oligonucleotides for binding to the first target nucleic acid, amplifying the first target nucleic acid with the polymerase chain reaction, thereby degrading the first signal oligonucleotide and permitting generation of a first signal, generating the first signal, measuring intensity of the first signal, and correlating the intensity of the first signal to the first ratio, thereby identifying the first target nucleic acid.

11 Claims, 6 Drawing Sheets

(56) References Cited

OTHER PUBLICATIONS

Rajagopal, Aditya et al. Unpublished U.S. Appl. No. 15/892,245, filed Feb. 8, 2018.
U.S. Appl. No. 15/892,245 Pre-interview First Interview Office Action dated May 11, 2018.
Yang, L. et al. A novel universal real-time PCR system using the attached universal duplex probes for quantitative analysis of nucleic acids. BMC Molecular Biology, 9:54 (1-13) Jun. 4, 2008.
Zhang, et al. A novel real-time quantitative PCR method using attached universal template probe. Nucleic Acids Res. Oct. 15, 2003;31(20):e123(pp. 1-8).
Blacket et al. Universal primers for fluorescent labeling of PCR fragments—an efficient and cost-effective approach to genotyping by fluorescence. Moleular Ecology Resources 12(3):456-463 (2012) Epub Jan. 24, 2012.
U.S. Appl. No. 15/892,245 First Action Interview—Office Action dated Jul. 19, 2018.

US 10,301,668 B2

COMPETITIVE PROBES FOR ENGINEERING SIGNAL GENERATION

CROSS-REFERENCE

This application is a continuation application of International Application No. PCT/US2017/024933, filed Mar. 30, 2017, which claims the benefit of U.S. Provisional Patent Application No. 62/317,151, filed Apr. 1, 2016, each of which are hereby incorporated by reference in their entirety.

BACKGROUND

Real-Time PCR is a process of monitoring a PCR reaction by recording the fluorescence generated either by an intercalating dye such as SYBR Green or a target-specific reporter probe at each cycle. This is generally performed on a Real-Time PCR instrument that executes thermal cycling of the sample to complete the PCR cycles and at a specified point in each cycle measures the fluorescence of the sample in each channel through a series of excitation/emission filter sets.

In the age of whole genome sequencing and high-throughput analysis, there is a need for methods of detecting multiple qPCR targets at once. A limitation of current qPCR machines is the number of channels available for target detection. Modern instruments have between two and six channels, meaning that only two to six reporters can be detected in each experiment. Contemporary multiplexing technology provides for two to four different fluorescent reporters, and therefore two to four targets, to be detected in a single reaction. Unfortunately, accurately distinguishing each of the two to four targets from one another is thwarted by overlapping fluorescence signals of the different reporters. Therefore, a need still remains for a reliable and precise method for distinguishing multiple reporter signals during multiplex qPCR reactions.

SUMMARY

The real-time polymerase chain reaction or quantitative PCR (qPCR) is a common molecular biology technique that uses fluorescent reporters to monitor the progress of the exponential amplification of target nucleic acids in a reaction. Traditionally the process is limited to differentiating the presence of one target per fluorescent emission filter (color channel) on a qPCR instrument.

Recent advances made at the California Institute of Technology nanofabrication lab allow for detection of multiple analytes per emission filter using mathematical algorithms on real-time PCR amplification curve characteristics such as amplitude and curve shape (U.S. Pat. No. 8,838,394 issued Sep. 16, 2014 and US Patent Application Publication Number US2015-0057178 published Feb. 26, 2015, both of which are incorporated herein in their entirety). Targets in the same color channel are "coded" to exhibit these amplification curve characteristics. Coding includes setting the intensity level of each target in a color channel.

Disclosed herein are methods by which the effective relative fluorescent intensity generated by a qPCR probe is adjusted independent of the total probe concentration for each target. This is a key improvement to the multi-analyte coding technique.

Disclosed herein are methods and compositions for uniquely and unambiguously detecting multiple targets in a single color detection channel. One aspect of the disclosed methods is the ability to differentiate multiple targets by ratio-metric coding of signal intensity (brightness) of any given color for each target and mathematical strategies to circumvent degeneracy. When used within each of the available color channels on a qPCR instrument, the disclosed methods significantly increase the number of target measurements that can be interrogated.

Provided herein are methods of identifying a first target nucleic acid comprising, providing a sample comprising the first target nucleic acid, providing a first set of paired oligonucleotides with complementarity to the first target nucleic acid, said first set of paired oligonucleotides comprising a first ratio of (a) first competitive oligonucleotides to (b) first signal oligonucleotides comprising a first signal tag, wherein the first competitive oligonucleotides compete with the first signal oligonucleotides for binding to the first target nucleic acid, amplifying the first target nucleic acid with the polymerase chain reaction, thereby degrading the first signal oligonucleotide and permitting generation of a first signal, generating the first signal, measuring intensity of the first signal, and correlating the intensity of the first signal to the first ratio, thereby identifying the first target nucleic acid. In some aspects, the sample comprises a second target nucleic acid. In some aspects, the method further comprises identifying the second target nucleic acid by providing a second set of paired oligonucleotides with complementarity to the second target nucleic acid, said second set of paired oligonucleotides comprising a second ratio of (a) second competitive oligonucleotides to (b) second signal oligonucleotides comprising a second signal tag, wherein the second competitive oligonucleotides compete with the second signal oligonucleotides for binding to the second target nucleic acid, amplifying the second target sequence with the polymerase chain reaction, thereby degrading the second signal oligonucleotide and permitting generation of a second signal, generating the second signal, measuring intensity of the second signal, and correlating the intensity of the second signal to the second ratio, thereby identifying the second target nucleic acid. In some aspects, the first signal oligonucleotides and the second signal oligonucleotides comprise the same signal tag. In some aspects, the first target nucleic acid and the second target nucleic acid are identified from differing signal intensities generated during the same polymerase chain reaction. In some aspects, the first signal intensity is different from the second signal intensity. In some aspects, the paired oligonucleotides comprise qPCR probes. In some aspects, the signal oligonucleotides comprise a signal tag and a signal quenching tag. In some aspects, the signal tag comprises a fluorophore. In some aspects, the signal quenching tag blocks the generation of the signal corresponding with the signal tag until the signal quenching tag is separated from the signal tag by oligonucleotide degradation during the polymerase chain reaction, thereby permitting the signal to be generated. In some aspects, generating the signal comprises exciting the signal tag. In some aspects, exciting comprises directing at the signal tag at least one of illumination, electromagnetic radiation, and energy emitted from an energy source. In some aspects, the competitive oligonucleotides do not comprise a signal tag. In some aspects, the competitive oligonucleotides comprise at least one modified end. In some aspects, the modified end prevents enzymatic extension during amplification. In some aspects, the modified end comprises a 3' end lacking a hydroxyl group. In some aspects, the modified end comprises a 5' end lacking a phosphate group. In some aspects, the modified end comprises a 5' capped end. In some aspects, the modified end comprises a 3' capped end. In some aspects, the ratio of signal oligonucleotides to competitive oligonucleotides or the ratio of competitive oligonucleotides to signal oligonucleotides is about 1:1. In some aspects, the ratio of signal oligonucleotides to competitive oligonucleotides or the ratio of competitive oligonucleotides to signal oligonucleotides is about 1:2. In some aspects, the ratio of signal oligonucleotides to competitive oligonucleotides or the ratio of competitive oligonucleotides to signal oligonucleotides is about 1:3. In some aspects, the ratio of signal oligonucleotides to competitive oligonucleotides or the ratio of competitive oligonucleotides to signal oligonucleotides is about 1:4. In some aspects, the ratio of signal oligonucleotides to competitive oligonucleotides or the ratio of competitive oligonucleotides to signal oligonucleotides is about 1:5. In some aspects, the ratio of signal oligonucleotides to competitive oligonucleotides or the ratio of competitive oligonucleotides to signal oligonucleotides is about 1:6. In some aspects, the ratio of signal oligonucleotides to competitive oligonucleotides or the ratio of competitive oligonucleotides to signal oligonucleotides is about 1:7. In some aspects, the ratio of signal oligonucleotides to competitive oligonucleotides or the ratio of competitive oligonucleotides to signal oligonucleotides is about 1:8. In some aspects, the ratio of signal oligonucleotides to competitive oligonucleotides or the ratio of competitive oligonucleotides to signal oligonucleotides is about 1:9. In some aspects, the ratio of signal oligonucleotides to competitive oligonucleotides or the ratio of competitive oligonucleotides to signal oligonucleotides is about 1:10. In some aspects, the ratio of signal oligonucleotides to competitive oligonucleotides or the ratio of competitive oligonucleotides to signal oligonucleotides is about 1:16. In some aspects, the ratio of signal oligonucleotides to competitive oligonucleotides or the ratio of competitive oligonucleotides to signal oligonucleotides is about 1:20. In some aspects, the paired oligonucleotides comprise only signal oligonucleotides or only competitive oligonucleotides. In some aspects, the total concentration of the first set of paired oligonucleotides is the same as the total concentration of the second set of paired oligonucleotides. In some aspects, the methods further comprise identifying up to thirty target nucleic acid sequences using up to thirty sets of paired oligonucleotides, wherein each set of paired oligonucleotides possesses complementarity to one of the up to thirty target nucleic acid sequences, wherein each of the up to thirty sets of paired oligonucleotides comprises a unique ratio of (a) competitive oligonucleotides to (b) signal oligonucleotides comprising a signal tag, wherein the competitive oligonucleotides within each set compete with the signal oligonucleotides within the same set for binding to a corresponding target nucleic acid sequence, amplifying the up to thirty target nucleic acid sequences with the polymerase chain reaction, thereby degrading the signal oligonucleotides and permitting generation of up to thirty signals, generating up to thirty signals, measuring the intensities of the up to thirty signals, and correlating the intensities of the up to thirty signals to the up to thirty ratios, thereby identifying the up to thirty target nucleic acid sequences. In some aspects, the signal tag of the signal oligonucleotides within each of the up to thirty sets of paired oligonucleotides are the same In some aspects, the up to thirty target nucleic acid sequences are identified from signal intensities generated during the same polymerase chain reaction. In some aspects, each of the up to thirty ratios differs from every other of the up to thirty ratios. In some aspects, each of the up to thirty signal intensities differs from every other of the up to thirty signal intensities In some aspects, the polymerase chain reaction is carried out by use of a nucleic acid polymerase having 5' to 3' exonuclease activity, an exopolymerase, or a molecular beacon. In some aspects, the up to five signals are measured in a single fluorescence channel. In some aspects, the total concentration of each of the up to five sets of paired oligonucleotides is the same. In some aspects, a total number of molecules in the reaction remains constant Provided herein are compositions comprising a first set of paired oligonucleotides with complementarity to a first target nucleic acid, said first set of paired oligonucleotides comprising a first ratio of (a) competitive oligonucleotides to (b) signal oligonucleotides comprising a signal tag, wherein the competitive oligonucleotides are configured to compete with the signal oligonucleotides for binding to the first target nucleic acid during amplification of the first target nucleic acid with the polymerase chain reaction, wherein the signal oligonucleotides are adapted to generate a first signal having a first intensity when degraded by a nucleic acid polymerase during the polymerase chain reaction and excited by an energy source, and wherein the first intensity correlates with the first ratio.

Provided herein are methods of identifying a first target molecule comprising, providing a sample comprising the first target molecule, providing a first set of paired capture molecules that bind to the first target molecule, said first set of paired capture molecules comprising a first ratio of (a) first competitive capture molecules to (b) first signal capture molecules comprising a signal tag, wherein the competitive capture molecules compete with the signal capture molecules for binding to the first target molecule, generating the first signal, measuring intensity of the first signal, and correlating the intensity of the first signal to the first ratio, thereby identifying the first target molecule. In some aspects, the sample comprises a second target molecule. In some aspects, the methods further comprise identifying the second target molecule by providing a second set of paired capture molecules that binds to the second target molecule, said second set of paired capture molecules comprising a second ratio of (a) second competitive capture molecules to (b) second signal capture molecules comprising the signal tag, wherein the second competitive capture molecules compete with the second signal capture molecules for binding to the second target molecule, generating the second signal, measuring intensity of the second signal, and correlating the intensity of the second signal to the second ratio, thereby identifying the second target molecule. In some aspects, the first signal capture molecules and the second signal capture molecules comprise the same signal tag. In some aspects, the first target capture molecules and the second target capture molecules are identified from differing signal intensities generated. In some aspects, the first signal intensity is different from the second signal intensity. In some aspects, the signal tag comprises a fluorophore. In some aspects, generating the signal comprises exciting the signal tag. In some aspects, exciting comprises directing at the signal tag at least one of illumination, electromagnetic radiation, and energy emitted from an energy source. In some aspects, the competitive capture molecules do not comprise a signaling tag. In some aspects, the ratio of signal capture molecules to competitive capture molecules or the ratio of competitive capture molecules to signal capture molecules is about 1:1 In some aspects, the ratio of signal capture molecules to competitive capture molecules or the ratio of competitive capture molecules to signal capture molecules is about 1:2. In some aspects, the ratio of signal capture molecules to competitive capture molecules or the ratio of competitive capture molecules to signal capture molecules is about 1:3.

In some aspects, the ratio of signal capture molecules to competitive capture molecules or the ratio of competitive capture molecules to signal capture molecules is about 1:4. In some aspects, the ratio of signal capture molecules to competitive capture molecules or the ratio of competitive capture molecules to signal capture molecules is about 1:5. In some aspects, the ratio of signal capture molecules to competitive capture molecules or the ratio of competitive capture molecules to signal capture molecules is about 1:6. In some aspects, the ratio of signal capture molecules to competitive capture molecules or the ratio of competitive capture molecules to signal capture molecules is about 1:7. In some aspects, the ratio of signal capture molecules to competitive capture molecules or the ratio of competitive capture molecules to signal capture molecules is about 1:8. In some aspects, the ratio of signal capture molecules to competitive capture molecules or the ratio of competitive capture molecules to signal capture molecules is about 1:9. In some aspects, the ratio of signal capture molecules to competitive capture molecules or the ratio of competitive capture molecules to signal capture molecules is about 1:10. In some aspects, the ratio of signal capture molecules to competitive capture molecules or the ratio of competitive capture molecules to signal capture molecules is about 1:16. In some aspects, the ratio of signal capture molecules to competitive capture molecules or the ratio of competitive capture molecules to signal capture molecules is about 1:20. In some aspects, the first paired capture molecules comprise only signal capture molecules or only competitive capture molecules. In some aspects, the methods further comprise identifying up to one hundred target molecules using up to one hundred sets of paired capture molecules, wherein each set of paired capture molecules that binds to one of the up to one hundred target molecules, wherein each of the up to one hundred sets of paired capture molecules comprises a unique ratio of (a) competitive capture molecules to (b) signal capture molecules comprising a signal tag, wherein the competitive capture molecules within each set compete with the signal capture molecules within the same set for binding to a corresponding target molecule, generating up to one hundred signals, measuring the intensities of the up to one hundred signals, and correlating the intensities of the up to one hundred signals to the up to one hundred ratios, thereby identifying the up to one hundred target molecules. In some aspects, the signal tag of the signal capture molecules within each of the up to one hundred sets of capture molecules are the same. In some aspects, the up to one hundred target molecules are identified from signal intensities generated at the same time. In some aspects, each of the up to one hundred ratios differs from every other of the up to one hundred ratios. In some aspects, each of the up to one hundred signal intensities differs from every other of the up to one hundred signal intensities. In some aspects, the up to one hundred signals are measured in a single fluorescence channel. In some aspects, the target molecule is fixed to a surface. In some aspects, the capture molecule is fixed to a surface. In some aspects, the target molecule comprises a protein or a functional fragment thereof. In some aspects, the target molecule comprises an antigen. In some aspects, the target molecule comprises an aptamer. In some aspects, the target molecule comprises a nucleic acid. In some aspects, the capture molecule comprises a protein a protein or a functional fragment thereof. In some aspects, the capture molecule comprises an antibody a protein or a functional fragment thereof. In some aspects, the capture molecule comprises an aptamer. In some aspects, a total number of molecules in the reaction remains constant.

Provided herein are compositions comprising a first set of paired capture molecules with complementarity to a first target molecule, said first set of paired capture molecules comprising a first ratio of (a) competitive capture molecules to (b) signal capture molecules comprising a signal tag, wherein the competitive capture molecules are configured to compete with the signal capture molecules for binding to the target molecule, wherein the signal capture molecules are adapted to generate a first signal having a first intensity when excited by an energy source, and wherein the first intensity correlates with the first ratio. In some aspects, the target molecule comprises a protein or a functional fragment thereof. In some aspects, the target molecule comprises a antigen. In some aspects, the target molecule comprises a aptamer. In some aspects, the target molecule comprises a nucleic acid. In some aspects, the capture molecule comprises a protein or a functional fragment thereof. In some aspects, the capture molecule comprises an antibody or a functional fragment thereof. In some aspects, the capture molecule comprises an aptamer.

Provided herein are methods of altering amplification level of a target nucleic acid comprising, providing a sample comprising the target nucleic acid, providing a set of paired oligonucleotides with complementarity to the target nucleic acid, said set of paired oligonucleotides comprising a ratio of (a) competitive oligonucleotides to (b) functional oligonucleotides, wherein the competitive oligonucleotides compete with the functional oligonucleotides for binding to the target nucleic acid and are not extendible by a nucleic acid polymerase, wherein the functional oligonucleotides are extendible by a nucleic acid polymerase as primers for amplifying the target nucleic acid by the polymerase chain reaction (PCR), and amplifying the target nucleic acid with PCR. In some aspects, the competitive oligonucleotides comprise at least one modified end. In some aspects, the modified end prevents enzymatic extension during amplification. In some aspects, the modified end comprises a 3' end lacking a hydroxyl group. In some aspects, the modified end comprises a 5' end lacking a phosphate group. In some aspects, the modified end comprises a 5' capped end. In some aspects, the modified end comprises a 3' capped end. In some aspects, a total number of molecules in the reaction remains constant.

Provided herein are compositions comprising a set of paired oligonucleotides with complementarity to a target nucleic acid, said set of paired oligonucleotides comprising a ratio of (a) competitive oligonucleotides to (b) functional oligonucleotides, wherein the competitive oligonucleotides are configured to compete with the functional oligonucleotides for binding to the nucleic acid target during amplification of the first target nucleic acid with the polymerase chain reaction and are not extendible by a nucleic acid polymerase.

DETAILED DESCRIPTION

Figure 1:
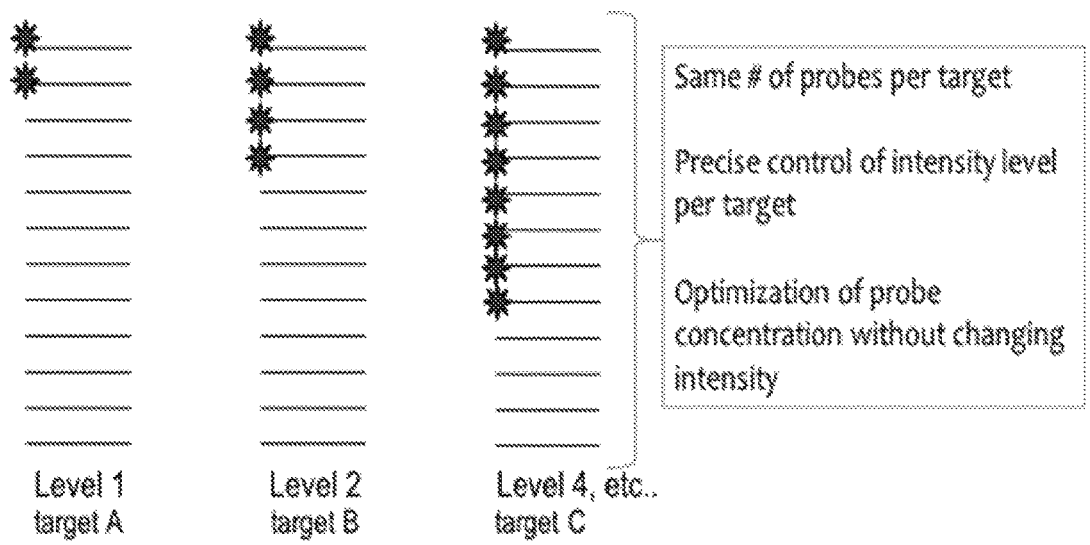
FIG. 1 illustrates three example probe sets with different ratios of competitive to fluorescent probes

Without being bound by theory, Polymerase Chain Reaction is a method of exponential amplification of specific target DNA in a reaction mix with a DNA polymerase and primers. Primers are short single stranded DNA oligonucleotides which are complementary to the 3' sequences of the positive and negative strand of the target sequence. The reaction mix is cycled in repeated heating and cooling steps. The heating cycle denatures or splits the double stranded DNA target into single stranded templates. In the cooling cycle, the primers bind to complementary sequence on the template. After the template is primed the DNA polymerase creates a copy of the original template. Repeated cycling exponentially amplifies the target 2 fold with each cycle leading to approximately a billion-fold increase of the target sequence in 30 cycles (Saiki et al 1988, Science 239: 487-491).

Real-Time PCR is a process of monitoring a PCR reaction by recording the fluorescence generated either by an intercalating dye such as SYBR Green or a target-specific reporter probe at each cycle. This is generally performed on a Real-Time PCR instrument that executes thermal cycling of the sample to complete the PCR cycles and at a specified point in each cycle measures the fluorescence of the sample in each channel through a series of excitation/emission filter sets Frequently, the target specific reporter probe is a short oligonucleotide complementary to one strand of the amplified target. The probe lacks a 3' hydroxyl and therefore is not extendable by the DNA polymerase. TaqMan (Thermo-Fisher Scientific) chemistry is a common reporter probe method used for multiplex Real-Time PCR (Holland et al. 1991). The TaqMan oligonucleotide probe is covalently modified with a fluorophore and a quenching tag. In this configuration the fluorescence generated by the fluorophore is quenched and is not detected by the real time PCR instrument. When the target of interest is present, the probe oligonucleotide base pairs with the amplified target. While bound, it is digested by the 5'→3' exonuclease activity of the Taq polymerase thereby physically separating the fluorophore from the quencher and liberating signal for detection by the real time PCR instrument. Other methods, such as molecular beacon probes, are also used in real-time PCR and amenable to this competitive probe technique.

For certain qPCR, multiplexed qPCR, and coded qPCR methods, there is a need to adjust signal level in a predictable fashion. This is typically done by increasing or decreasing the number of fluorometric reporters added to a reaction. While this does adjust signal level to the first order, it also risks altering the chemical behavior of the reaction mixture as the total number of participating reactants has also changed. Often, this adversely affects the performance of other components within the reaction mixture. In particular, this is a critical failure mode for multiplexed qPCR. Disclosed herein are methods and compositions for detecting multiple target sequences with the same fluorophore within a single coded or multiplexed qPCR reaction.

Disclosed herein are methods and compositions for adjusting fluorescent intensity without adjusting the reactant concentrations in a mixture. In some embodiments, combinations of both light-emitting and non-light-emitting chemical reporters are used to independently adjust the fluorescent intensity of a qPCR reaction without altering the chemical interactivity of the qPCR reaction mixture. In some embodiments, this is achieved by creating a mixture of non-fluorescent oligo probes and the TaqMan reporter probes for every target interrogated in a qPCR reaction.

The herein disclosed competitive probes (also referred to as dimming probes, or non-fluorescing probes) are oligonucleotides similar to target probes with the exception of the covalently attached fluorophore and quencher. In some embodiments, the competitive probes do not have the fluorophore or the quencher. In some embodiments, the competitive probes have capped 5' and 3' ends to prevent enzymatic extension. In some embodiments, the competitive probes have a 5' end lacking a phosphate group. In some embodiments, the competitive probes have a 3' end lacking a hydroxyl group. In general, competitive probes behave identically to the specific target probes in binding to the amplified target sequence, and in the case of TaqMan style assay, the bound probes are digested by the 5'→3' exonuclease activity of Taq polymerase. However, because the competitive probes do not contain a fluorophore, no signal is generated.

Disclosed herein are methods and compositions for using the disclosed non-fluorescing, competitive binding probes to adjust the signal intensity for a single gene by ratiometric titration of the competitive binding probe. In some examples, these methods are performed using a TaqMan probe. FIG. 1 diagrams three different probes mixtures with differing proportions of competitive probes and signal probes. In some embodiments, the titration of the intensity allows for control of intensity level ratio-metric coding and the ability to adjust the total probe concentration of a given target without affecting the intensity level coding.

In some embodiments, during the probe annealing portion of the PCR reaction the competitive probes will bind to the amplified target at a rate proportional to the ratio of competitive probes to the total probes both labeled and unlabeled in the reaction yielding a fluorescent signal proportional to the ratio of labeled probes to the total probes.

In some embodiments, the competitive probes are unextendable probes. For example, the competitive probes are unable to initiate DNA synthesis by the Taq polymerase by employing a variety of 3' modifications including but not limited to the phosphorylation or the addition of a quenching molecule.

In some embodiments, different purification methods and probe sequences are used to yield dramatically different fluorescence intensities. In some examples, differences in the quality of purification leads to more or less unlabeled product (similar to a competitive probe) reducing the fluorescence of a preparation. In some embodiments, the oligo sequence makeup of a probe affects the fluorescence, particularly guanine bases proximal to the fluorophore which can act as a quencher reducing the intensity of fluorescence. In some embodiments, the competitive probes are used to adjust the signal intensity to be consistent between preparations for more consistent lot to lot performance. In some embodiments, competitive probes are used if a dye's intensity is overloading the detector on a particular real-time PCR instrument.

In some embodiments, competitive probes are used to engineer the optical characteristic of a PCR curve without altering its chemical characteristic. In some examples, this is achieved because competitive probes competitively interact with other sequences, along with their TaqMan probe equivalents. In these examples, this competitive interaction allows for the unique capability to fine tune the signal to noise of a PCR reaction without changing the chemical performance of the PCR itself.

Disclosed herein are methods and compositions for using competitive primers for multiplex quantitation by normalizing the efficiency of multiplexed reactions. In some embodiments, the herein disclosed methods are used to drive the PCR reaction into producing more of one strand than the other which can lead to an earlier plateau phase of the PCR reaction.

In some embodiments, competitive probes are used to replace a portion of priming oligonucleotides in a PCR reaction. In many of these examples, the competitive probes are rendered un-extendable by 3' phosphorylation or other methodology. In these cases, the competitive primer will compete with the extendable primer leading to a quantifiable fraction of template strands to fail to replicate during the extension phase of the PCR. One advantage of these embodiments is that it allows the adjustment of amplification efficiency of either one or both of the replication strands.

In some embodiments, the herein disclosed competitive probes are used in TaqMan style PCR. In some embodiments, the herein disclosed competitive probes are used in traditional PCR.

Disclosed herein are methods for identifying a target by detecting a corresponding signal, such as a fluorescent signal. In some examples, multiple targets can be detected in a single experiment, wherein the corresponding signal from each is the same. For example, multiple targets can be identified, where each target has a corresponding fluorescent signal, wherein the signal generating molecule, such as a fluorophore, is the same among each of the different targets to be detected.

Using methods disclosed herein, multiple targets can be detected using the same fluorophore by providing sets of target-binding molecules, such as probes, wherein each set of molecules comprises a unique ratio of competitive probes to signal probes. Signal probes can comprise a signal generating molecules, such as a fluorophore. Competitive probes often do not contain the signal generating molecule. In these cases, the total number of probes within each set of probes is the same, which the ratio of competitive probes to signal probes is unique for each target to be detected. This allows for the same level or concentration of total probes to be used for each target while still being able to distinguish each individual target.

Disclosed herein are methods and compositions for detecting multiple target sequences with the same fluorophore. Also disclosed herein are methods and compositions for detecting multiple target specific reporter signals in a single reaction using fluorophore baring oligonucleotide probes in combination with non-fluorophore baring oligonucleotide probes. In some examples, each target sequence is detected using a set of oligonucleotide probes. Each oligonucleotide set can comprise two populations of oligonucleotide probes, each comprising the same nucleic acid sequence. In these examples, one population of oligonucleotides comprises a reporter fluorophore while the second population of oligonucleotides does not comprise a fluorophore. In some embodiments, up to five sets of oligonucleotide probes are used to detect up to five target sequences in a single reaction. In many of these examples, the fluorophore of the up to five sets of probes is the same. In some aspects, within each set of oligonucleotide probes the ratio of fluorophore baring and non-fluorophore baring oligonucleotides is set to a predetermined ratio. In some embodiments, the ratio within each set of oligonucleotides is different for each of the up to five sets of oligonucleotides. In these examples, the different ratios allow the reporter signal for each of the up to five targets to be distinguished from one another within a single reaction. In these examples, the total concentration of probes in each set of probes is the same, while the ratio of the two populations of probes within the probe set are different between each of the sets of probes. A fluorophore baring probe can be a signal probe. A non-fluorophore baring probe can be a competitive probe.

In some embodiments, up to 100 sets of oligonucleotide probes are used to detect up to 100 target sequences in a single reaction. For example, there can be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 sets of oligonucleotide probes used to detect 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 target sequences in a single reaction. In many of these examples, the fluorophore of the up to 100 sets of probes is the same. In some aspects, within each set of oligonucleotide probes the ratio of fluorophore baring and non-fluorophore baring oligonucleotides is set to a predetermined ratio. In some embodiments, the ratio within each set of oligonucleotides is different for each of the up to 100 sets of oligonucleotides. In these examples, the different ratios allow the reporter signal for each of the up to 100 targets to be distinguished from one another within a single reaction. In these examples, the total concentration of probes in each set of probes is the same, while the ratio of the two populations of probes within the probe set are different between each of the sets of probes. A fluorophore baring probe can be a signal probe. A non-fluorophore baring probe can be a competitive probe.

In some embodiments greater than 100 oligonucleotide probes are used to detect greater than 100 target sequences in a single reaction. In some embodiments, greater than 100 oligonucleotide probes are used to detect up to 100 target sequences in a single reaction. In some embodiments, up to 100 oligonucleotide probes are used to detect greater than 100 target sequences in a single reaction.

Disclosed herein are methods and compositions for using an unlabeled analog to the corresponding labeled entity that generates signal for detection in the presence of a particular analyte in any system. In some examples, the system is an ELISA (enzyme-linked immunosorbent assay), in which case the labeled entity is a labeled antibody. In these cases, the unlabeled analog is an unlabeled antibody. In some embodiments, the ratio of labeled and unlabeled antibodies within a target set are predetermined as discussed previously. In some embodiments, multiple targets can be detected in a single ELISA reaction using multiple target sets of antibodies. In many of these examples, each set of target antibodies has a different ratio of labeled and unlabeled antibodies which allow the independent target reporting signal to be distinguished from the others. In these examples, the total concentration of antibodies in each set of antibodies is the same, while the ratio of the two populations of antibodies within the antibodies set are different between each of the sets of antibodies. A fluorophore baring antibody can be a signal antibody. A non-fluorophore baring antibody can be a competitive antibody.

In some embodiments, the total number of molecules in a reaction remains constant despite that the ratio of functional to competitive entities changes between different sets. In some aspects, the total number of molecules refers to the proteins, nucleic acids, solution volume, other entities required for the reaction to take place. In some aspects the reaction is a qPCR, ELISA, PCR, or sequencing reaction. In some aspects, the entities are oligonucleotides, proteins, antibodies, qPCR probes, aptamers, nucleic acid or other appropriate molecule. In some aspects function al comprises performing its intended purpose, such as PCR extension or emitting of fluorescence signal. In some aspects, competitive comprises binding to the target molecule, whether that be a protein, nucleic acid, or another molecule, but not being able to perform the function of the function molecule, such as extend during PCR or emit a fluorescence signal when excited.

Antibody Labeling

ELISA is a standard analytical technique for identifying proteins using fluorescence-labelled antibody markers. Without being bound by theory, in a sandwich ELISA, two antibodies, a primary antibody and a fluorescently labeled secondary antibody, are used to bind and identify a protein of interest (antigen). In general, the two antibodies bind to distinct regions of the protein. The primary antibody is adhered to a surface or a reaction vessel, with its binding domain exposed to allow for protein capture. When a sample is introduced, the protein of interest will diffuse through the chamber and favorably bind to the primary antibody. After a wash procedure, the fluorescently labeled secondary antibody is introduced. This fluorescently labeled secondary antibody binds to a distinct epitope of the fixed antigen. After washing the excess, unbound secondary antibody, the sample is interrogated. The presence and intensity of the fluorescence signal correlates with the concentration of antigen that has been captured. However, the binding dynamics of the antibodies are not readily engineerable. Unlike nucleic acids, antibodies cannot be inorganically assembled and even simple changes to the antibody structure result in dramatic changes in binding efficiencies. This critically limits the efficiency of antibody multiplexing for ELISA.

Disclosed herein are methods and compositions for using competitive, non-reporting probes for fluorescence reporting using antibodies. In some embodiments, the fluorescence reporting is in the context of an ELISA assay. In some embodiments, a primary antibody is adhered to a surface or a reaction vessel and the protein of interest favorably binds to the primary antibody. In these cases, after a wash procedure, a fluorescently labeled secondary antibody is introduced and binds to a distinct epitope of the fixed antigen. In these cases, after a wash procedure, the sample is interrogated and the presence and intensity of the fluorescence signal correlates with the concentration of antigen that has been captured.

In some embodiments, a set of secondary antibodies is introduced and binds to the fixed antigen. In some aspects, the antigen is fixed by being bound to a primary antibody, which is in turn adhered to a surface or a reaction vessel. In some aspects, the set of secondary antibodies comprises a labeled population and an unlabeled population. In some aspects, the secondary antibodies in the labeled and unlabeled populations are identical except for the presence or absence of the label. In some aspects, secondary antibodies being identical means they comprise the same protein sequence. In some aspects, identical means they bind to the same epitope. In some aspects, identical means they bind to the same antigen. In some embodiments, the label is a fluorescent label. In some embodiments, the ratio of labeled and unlabeled secondary antibodies within a set of secondary antibodies is set to a predetermined ratio. In some aspects, the ratio of labeled to unlabeled secondary antibodies correlated to a signal intensity. In some aspects, by measuring the signal intensity, the signal intensity can be correlated back to the ratio of labeled to unlabeled secondary antibodies.

In some embodiments, the ratio of labeled to unlabeled secondary antibodies within a set of secondary antibodies is used to set the signal level for an ELISA immunoassay. In some aspects, the ratio is set without changing the sensitivity or the number of antigens captured. In some embodiments, the primary antibody determines capture sensitivity and sensitivity. In some embodiments, multiple distinct antigens can be detected in a single ELISA reaction using the methods disclosed herein. In some aspects, a set of secondary antibodies able to bind to each of the multiple antigens is used in the ELISA. In many cases, the same label is used to label the labeled secondary antibody within each of the multiple sets of secondary antibodies. In some aspects the ratio of labeled to unlabeled secondary antibodies is unique within each of the multiple sets of secondary antibodies. In many examples, the unique ratios correspond to unique signal intensities. In these and other examples, the unique signal intensities are measured and correlated back to the predetermined ratios, thereby identifying the set of secondary antibodies that generated the signal intensity. In this way, a specific antigen can be identified in an ELISA assay based on the unique signal generated by the unique ratio of labeled to unlabeled secondary antibodies within the unique set of secondary antibodies used to bind to the specific antigen. In many examples, these methods disclosed herein allow identification of multiple antigens despite using the same label on the labeled secondary antibodies for each of the multiple antigens. This is achieved by using unique ratios of labeled to unlabeled secondary antibodies for each of the multiple antigens. The unique ratios correlate to unique signal intensities, thereby allowing identification of each of the multiple antigens.

Sequencing Bias

While genomic sequencing is poised to be the predominant clinical tool in the coming future, it has particularly susceptible to sample-preparation bias. Without being bound by theory, before nucleic acids are sequenced, they are enriched using highly multiplexed broad-binding PCR primers. However, this enrichment generates a large bias in the amplified targets. This bias results in ineffective sequencing. For applications such as cancer tissue genotyping and tumor heterogeneity assessment, this makes the technique inapplicable for many clinical use cases.

Disclosed herein are methods and compositions for using competitive oligonucleotides to reduce sequencing bias. In some embodiments, sequencing bias is reduced by using a set of oligonucleotide primers during amplification. In some aspects, amplification comprises a polymerase chain reaction. In some embodiments, a set of primers comprises a population of functional primers and a population of competitive primers. In some aspects, functional primers comprise primers capable of annealing to a complementary sequence and being extended during a polymerase chain reaction. In some aspects, competitive primers comprise are identical in sequence to their corresponding functional primer, are able to bind to the same complementary sequence, but are not able to be extended during a polymerase chain reaction. In some embodiments, the ratio of functional and competitive primers is adjusted to alter the level of sequencing bias without changing the chemical interactivity of the primer sets themselves. In some embodiments, reducing or increasing the ratio of functional primers to competitive primers, increase or decrease the enrichment of DNA to be sequenced. In some aspects, this ratio adjustment is performed without affecting the enrichment of other portions of the genome. In some aspects, this ratio adjustment allows a fine control of PCR bias. In some aspects, this ratio adjustment allows for the compensation of the deficiencies of current PCR methods for sequencing prep.

In some embodiments, the ratio of functional primers to competitive primers is increased. In some aspects, the ratio of functional primers to competitive primers is increased in order to increase the sequencing bias of a target sequence. In some aspects, altering sequencing bias comprises increasing the amplification level of the target sequence. In some aspects, increasing the amplification level of the target sequence leads to an increased level of the target sequence in the final sample to be sequenced.

In some embodiments, the ratio of functional primers to competitive primers is decreased. In some aspects, the ratio of functional primers to competitive primers is decreased in order to decrease the sequencing bias of a target sequence. In some aspects, altering sequencing bias comprises decreasing the amplification level of the target sequence. In some aspects, decreasing the amplification level of the target sequence leads to an decreased level of the target sequence in the final sample to be sequenced.

In some embodiments, competitive primers are not able to be extended. In some aspects, they are not able to be extended due to a competitive, capped, or otherwise modified end, such as those described and disclosed herein.

EXAMPLES

Example 1

Figure 2:
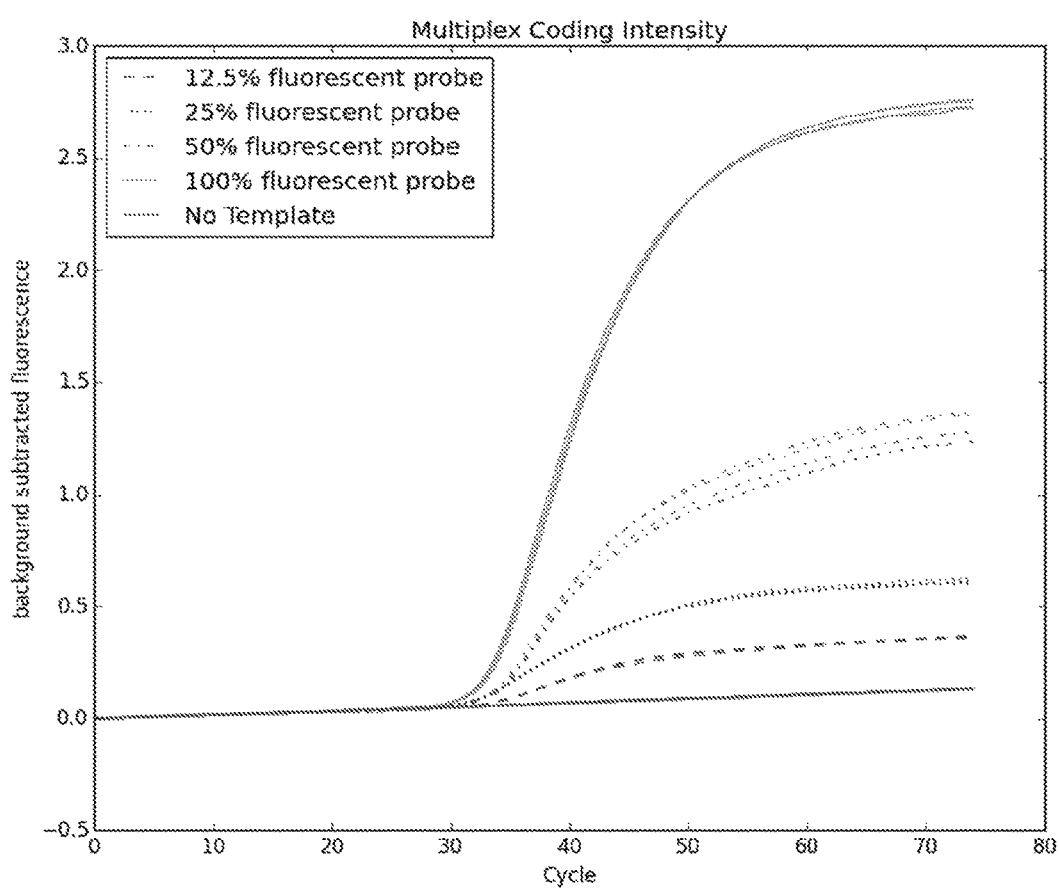
FIG. 2 illustrates an example PIV3 benchmark assay titration performed at four distinct coding levels.

A Real-Time PCR reaction with an equimolar ratio of competitive probes and fluorogenic probes would yield approximately half the fluorescent signal at each reading as compared to a reaction with a similar amount of fluorogenic probes. FIG. 2 shows the same TaqMan Assay with 4 differing proportions of fluorogenic probes to total probes. The 100% fluorescent probe reaction in yellow (solid top line) has an amplitude approximately 8 fold that of the assay in grey (long dashed line) which has 1 part fluorescent probes with 7 parts competitive probes. See Table 1 for the reaction make up and Table 2 for the PCR cycling parameters.

TABLE 1

Reaction components for FIG. 2 reactions

| Reaction Mix | Part # | 12.5% fluorescent probe | 25% fluorescent probe | 50% fluorescent probe | 100% fluorescent probe | No Template |
|---|---|---|---|---|---|---|
| ABI TaqMan Universal Master Mix | 4304437 | 10 µL | 11 µL | 12 µL | 13 µL | 14 µL |
| Ambion Nuclease Free Water | AM9937 | 4 µL | 4 µL | 4 µL | 4 µL | 4 µL |
| Promega TE 1× (diluant) | V6231 | 6 µL | 6 µL | 6 µL | 6 µL | 6 µL |
| Oligo (concentration in final reaction) | | | | | | |
| Forward Primer 1 | FBF2 | 200 nM | 200 nM | 200 nM | 200 nM | 200 nM |
| Reverse Primer 1 | FBR2 | 200 nM | 200 nM | 200 nM | 200 nM | 200 nM |
| FAM Labeled Probe 1 | FBP2-1 | 25 nM | 25 nM | 25 nM | 25 nM | 25 nM |
| Blunt Probe 1 | FBP2-0 | 175 nM | 175 nM | 175 nM | 175 nM | 175 nM |
| Forward Primer 2 | FAF1 | 200 nM | 200 nM | 200 nM | 200 nM | 200 nM |
| Reverse Primer 2 | FAR1 | 200 nM | 200 nM | 200 nM | 200 nM | 200 nM |
| FAM Labeled Probe 2 | FAP1-1 | 50 nM | 50 nM | 50 nM | 50 nM | 50 nM |
| Blunt Probe 2 | FAP1-0 | 150 nM | 150 nM | 150 nM | 150 nM | 150 nM |
| Forward Primer 3 | RBF 1 | 200 nM | 200 nM | 200 nM | 200 nM | 200 nM |
| Reverse Primer 3 | RBR1 | 200 nM | 200 nM | 200 nM | 200 nM | 200 nM |
| FAM Labeled Probe 3 | RBP1-1 | 100 nM | 100 nM | 100 nM | 100 nM | 100 nM |
| Forward Primer 4 | RBP1-0 | 100 nM | 100 nM | 100 nM | 100 nM | 100 nM |
| Reverse Primer 4 | RAF2 | 200 nM | 200 nM | 200 nM | 200 nM | 200 nM |
| FAM Labeled Probe 4 | RAR2 | 200 nM | 200 nM | 200 nM | 200 nM | 200 nM |
| Blunt Probe 4 | RAP2-1 | 200 nM | 200 nM | 200 nM | 200 nM | 200 nM |

TABLE 1-continued

Reaction components for FIG. 2 reactions

| Reaction Mix | Part # | 12.5% fluorescent probe | 25% fluorescent probe | 50% fluorescent probe | 100% fluorescent probe | No Template |
|---|---|---|---|---|---|---|
| template (copies per reaction) | | | | | | |
| Template 1 | FBT2 | 1000 copies | — | — | — | — |
| Template 2 | FAT1 | — | 1000 copies | — | — | — |
| Template 3 | RBT1 | — | — | 1000 copies | — | — |
| Template 4 | RAT2 | — | — | — | 1000 copies | — |
| total volume [μL] | | 20 μL | 20 μL | 20 μL | 20 μL | 20 μL |

TABLE 2

Temperature Schedule on ABI Viia7 for FIG. 2 reactions

| Temperature Schedule: | Temperature [° C.] | Time [s] | Data Collection |
|---|---|---|---|
| UNGase | 50 | 120 | N |
| Initial Denature | 95 | 600 | N |
| Number of Cycles | 75 | | |
| Denature | 95 | 15 | N |
| Anneal | 60 | 30 | Y |

Example 2

A Real-Time PCR reaction is performed to detect three nucleic acid sequences of interest within a single reaction. In addition to the other components required for the RT-PCR reaction, three sets of probes are added. One of each of the sets of probed corresponds to and is able to uniquely bind to one of the three transcripts of interest.

Set 1 comprises 25% unlabeled competitive probes and 75% labeled probes, which are labeled with a green fluorophore and a quencher molecule. The probes within Set 1 are identical other than the presence of the fluorescent label and quencher molecule.

Set 2 comprises 50% unlabeled competitive probes and 50% labeled probes, which are labeled with a green fluorophore and a quencher molecule. The probes within Set 2 are identical other than the presence of the fluorescent label and quencher molecule. The green fluorophore used in Set 2 is the same green fluorophore used in Set 1.

Set 3 comprises 75% unlabeled competitive probes and 25% labeled probes, which are labeled with a green fluorophore and a quencher molecule. The probes within Set 3 are identical other than the presence of the fluorescent label and quencher molecule. The green fluorophore used in Set 3 is the same green fluorophore used in Set 1 and Set 2.

The probes within each of Sets 1-3 are distinct from each other since they are selected for their ability to specifically bind to their corresponding nucleic acid target. However, the fluorophore used to label the labeled probes within each set is the same. Also, the ratio of unlabeled to labeled probes within each set are different and unique compared to the other sets.

When the reaction first starts, no fluorescent signal is detected since the signals from each fluorophore are blocked by the quencher molecule. As the reaction proceeds, unlabeled and labeled probes within each set compete for binding to their complementary nucleic acid target sequence. Because the labeled and unlabeled probes within each set are basically identical, their binding and annealing kinetics are basically identical. When a labeled probe anneals, it is subsequently degraded by the 5' to 3' exonuclease activity of the polymerase. This degradation step separates the fluorophore and the quenching molecule, allowing for a fluorescence signal to be emitted upon excitation by the appropriate excitation source.

An excitation source excites the green fluorophores and a signal is emitted from each of the released green fluorophores. Three distinct signal intensities are detected and measured. Each signal intensity correlated to a specific ratio. Because each set of probes comprised a unique ratio of labeled to unlabeled probes, a unique signal intensity can be correlated to that specific set of probes. Therefore, each unique signal intensity is used to identify one of each of the three nucleic acid targets.

Example 3

Figure 3A:
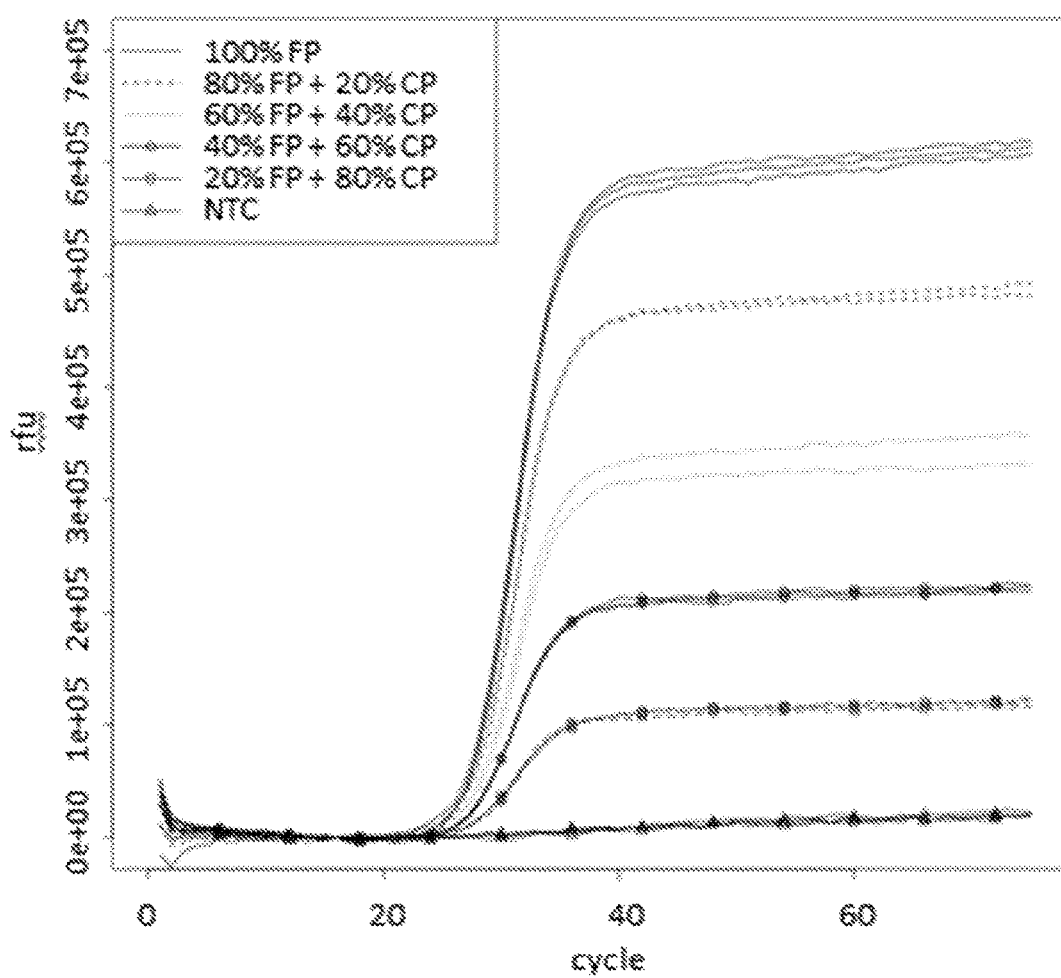
FIGS. 3A-3B illustrate an example RT-qPCR experiment with five distinct ratio levels of labeled and unlabeled competitive probes.
Figure 3B:
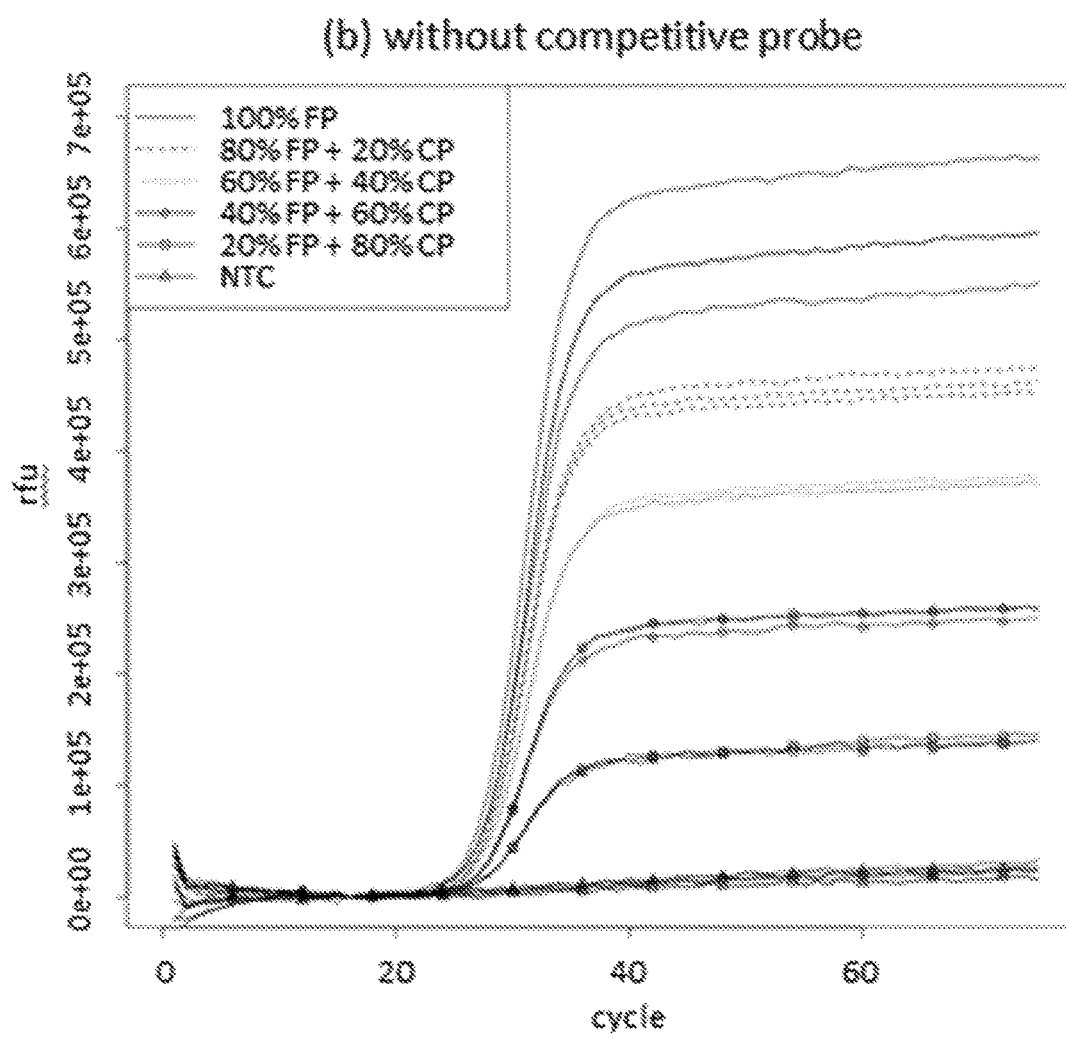

FIGS. 3A and 3B demonstrate an example experiment exemplifying consistent leveling with competitive probes versus diluted probes.

Ten RT-qPCR Master Mixes were made for a system containing three TaqMan™ assays in a single color channel for human rhinovirus, respiratory syncytial virus A (RSV A), and respiratory syncytial virus B (RSV B). All three assays utilized probes with the same fluorophore quencher combination. The total probe concentration of the mixtures was conserved for five of these reactions. Table 3 summarizes how the fluorescent and competitive probes were diluted to the same concentration. Table 4 summarizes how the primer sets were diluted to the same concentration. Table 5 displays the master mix composition for reactions containing both fluorescent and competitive probes. Table 5 displays the master mix composition for reactions containing fluorescent probes only with no competitive probes. Table 7 displays the concentration of the three templates included in each reaction.

The fluorescent probe concentrations for two of the targets (RSV A and RSV B) were fixed but different. For the final target (human rhinovirus, RH), the fluorescent probe concentration was varied from 25 nM. All reactions contained the same enzyme formulation and primer concentrations, as shown in Tables 5 and 6.

The qPCR protocol for each of the 10 master mixes were tested with known single-stranded DNA templates at DNA templates with a fixed concentration of 10,000 copies per reaction (Table 7). The qPCR reactions were performed on a standard qPCR instrument with the cycling parameters shown in Table 8. The resulting data is depicted in FIG. 3A and FIG. 3B.

TABLE 3

Oligo mix

| Oligo mix | Oligo | µM | Oligo volume to make 10x stock | TE Buffer | Total Volume |
|---|---|---|---|---|---|
| RH 100% Fluorescent | RHP1-1 | 101.1 | 2.47 | 997.53 | 1000.0 |
| RH 100% Competitive | RHP1-0 | 95.2 | 2.63 | 997.37 | 1000.0 |
| RSV B 100% Fluorescent | RBP1-1 | 101.1 | 2.24 | 997.76 | 1000.0 |
| RSV A 25% Fluorescent | RAP2-1 | 95.9 | 0.50 | 999.50 | 1000.0 |
| RSV A 75% Competitive | RAP2-0 | 93.8 | 2.00 | 998.00 | 1000.0 |

TABLE 4

6plex primer mix

| Primer set | Material | µM | Desired µM in 20X stock | Oligo volume to make 10x stock (µL) |
|---|---|---|---|---|
| Set 1 | cdcFAUniF1 | 93.1 | 0.4 | 17.19 |
|  | cdcFAUniR1 | 99.2 | 0.4 | 16.13 |
| Set 2 | ccFAH1_2009F2 | 117 | 0.4 | 13.68 |
|  | ccFAH1_2009R2 | 114 | 0.4 | 14.04 |
| Set 3 | cdcFAH3F3 | 114.6 | 0.4 | 13.96 |
|  | cdcFAH3R3 | 97.23 | 0.4 | 16.46 |
| Set 4 | RHF1 | 97.7 | 0.4 | 16.38 |
|  | RHR1 | 96.7 | 0.4 | 16.55 |
| Set 5 | RAF2 | 102.2 | 0.4 | 15.66 |
|  | RAR2 | 94.7 | 0.4 | 16.90 |
| Set 6 | RBF1 | 94.2 | 0.4 | 16.99 |
|  | RBR1 | 94.7 | 0.4 | 16.90 |
| Set 7 | RBF1 | 94.2 | 0.4 | 42.46 |
|  | RBR1 | 94.7 | 0.4 | 42.24 |
|  | Promega V6231, TE | n/a | n/a | 9.2 |

TABLE 5

Reaction Master Mix-with competitive probes

| Material | 100 FP | 80 FP + 20 CP | 60 FP + 40 CP | 40 FP + 60 CP | 20 FP + 80 CP |
|---|---|---|---|---|---|
| TaqPath ABI A28626 | 60 µL | 60 | 60 | 60 | 60 |
| 20X 6plex primer mix | 12 | 12 | 12 | 12 | 12 |
| 10X RH 100% Fluorescent | 24 | 19.2 | 14.4 | 9.6 | 4.8 |
| 10X RH Competitive | 0 | 4.8 | 9.6 | 14.4 | 19.2 |
| 10X RSV B 100% Fluorescent | 24 | 24 | 24 | 24 | 24 |
| 10X RSV A 25% Fluorescent | 24 | 24 | 24 | 24 | 24 |
| 10X RSV A Competitive | 24 | 24 | 24 | 24 | 24 |
| water RxBiosciences | 12 | 12 | 12 | 12 | 12 |

TABLE 6

Reaction Master Mix-without competitive probes

| Material | 100 FP-BP | 80 FP | 60 FP | 40 FP | 20 FP |
|---|---|---|---|---|---|
| TaqPath ABI A28626 | 60 µL | 60 | 60 | 60 | 60 |
| 20X 6plex primer mix | 12 | 12 | 12 | 12 | 12 |
| 10X RH 100% Fluorescent | 24 | 19.2 | 14.4 | 9.6 | 4.8 |
| 10X RSV B 100% Fluorescent | 24 | 24 | 24 | 24 | 24 |
| 10X RSV A 25% Fluorescent | 24 | 24 | 24 | 24 | 24 |
| water RxBiosciences | 12 | 12 | 12 | 12 | 12 |
| TE Promega V6231 | 24 | 28.8 | 33.6 | 38.4 | 43.2 |

TABLE 7

Templates

| Name | Concentration |
|---|---|
| RHT1 | 2E3 copies/µL |
| RAT2 | 2E3 copies/µL |
| RBT1 | 2E3 copies/µL |
| NTC TE | NA (buffer only) |

TABLE 8

Cycling Parameters

| Step | time(seconds) | temperature(° C.) | |
|---|---|---|---|
| 1 | 120 | 25 | |
| 2 | 600 | 53 | |
| 3 | 120 | 95 | |
| 4 | 3 | 95 | |
| 5 | 30 | 60 | detection |
| repeat step 4 & 5 90 cycles | | | |

Example 4

Figure 4A:
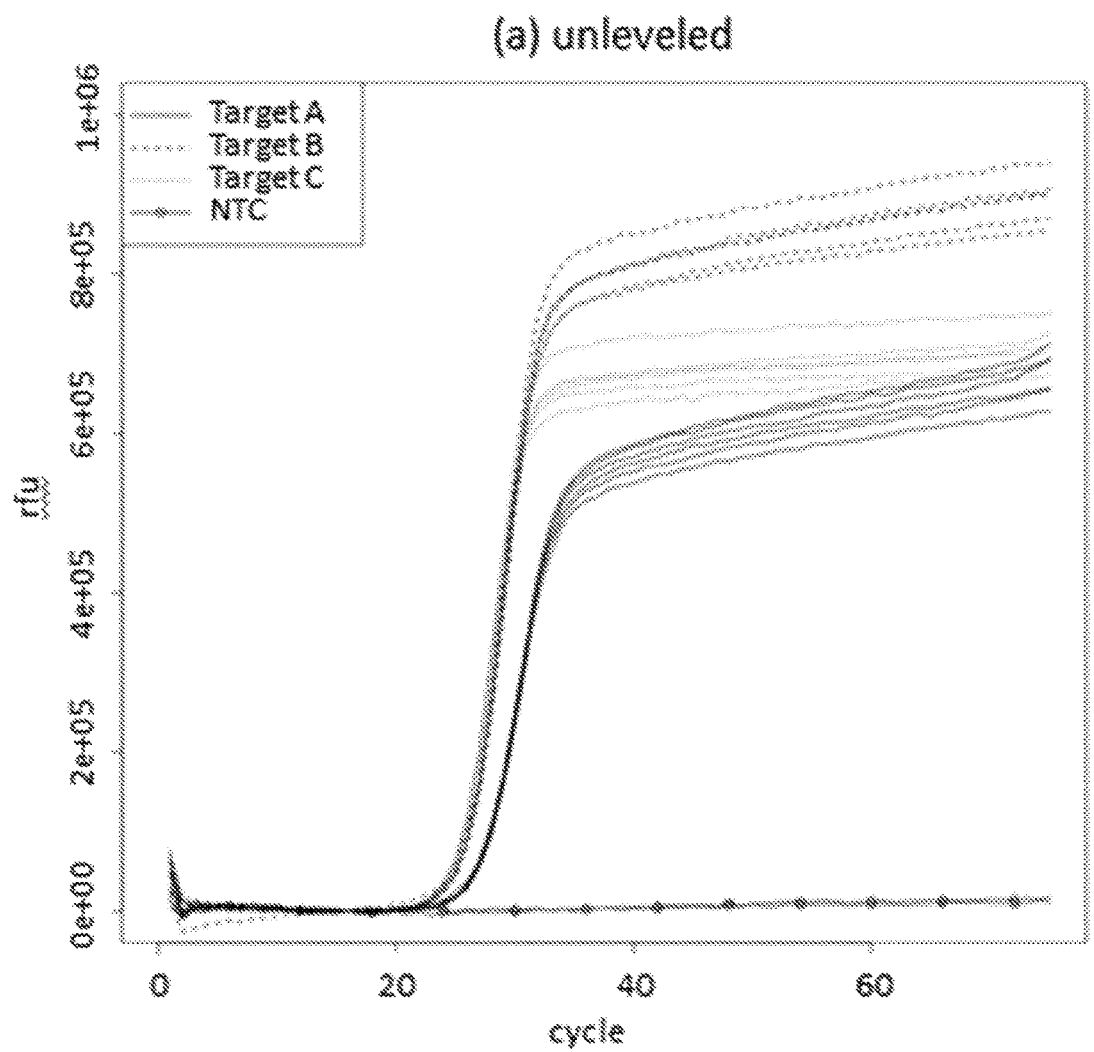
FIGS. 4A-4B illustrate an example RT-qPCR experiment with three distinct ration levels of labeled and unlabeled competitive probes.
Figure 4B:
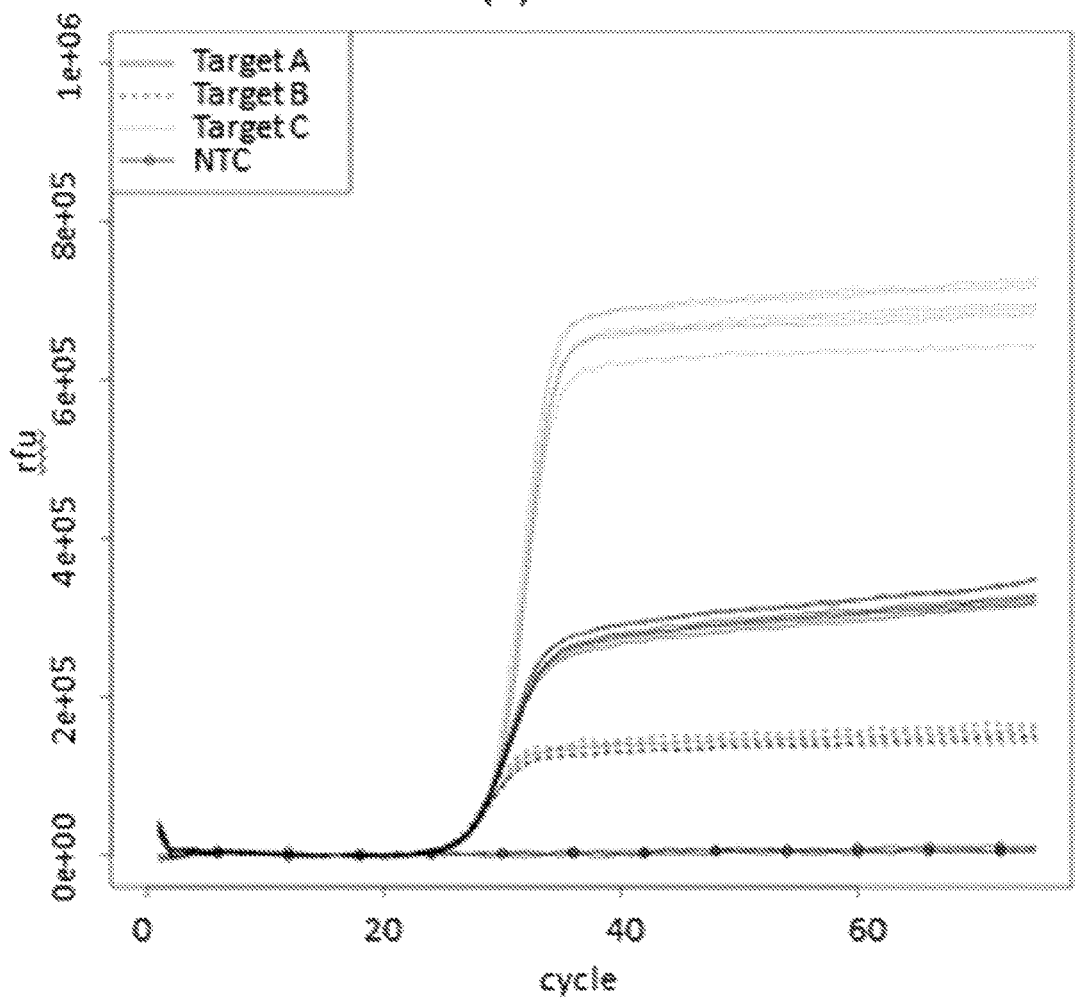

The following example experiments and resulting data displayed in FIG. 4A and FIG. 4B demonstrate the ability to deterministically generate a 3 plex assay with the same reporting fluorophore and quencher combination with the binary separation based upon initial 100% fluorescent probe data.

To generate the initial fluorescence data a RT-qPCR Master Mix was made containing three TaqMan™ assays for human rhinovirus (Target A), respiratory syncytial virus A (Target B) and respiratory syncytial virus B (Target C). No non-fluorescent, competitive probes were used in these assays. All three assays were labeled with the same fluorophore quencher combination. The primer concentration was selected to be in excess of the total probe concentration. The same concentration of fluorogenic probe, and therefore total probe, was used for each target.

Table 9 displays the composition of the oligo master mix, which contained the indicated fluorescent probes and no competitive probes. Table 10 displays the composition of the primer master mix. Table 11 displays the master mix composition for reactions containing only 100% fluorescent probes and no competitive probes. Table 12 displays the concentration of the three templates included in each reaction. Table 13 displays the cycling parameters used for the RT-qPCR reaction.

TABLE 9

25X fluorescence probe Oligo Mix

| Oligo Mix | Oligo | Stock Conc, μM | Conc. of 1x, μM | Vol, μL |
|---|---|---|---|---|
| Target A RH 100% Fluorescent | RHP1-1 | 79.9 | 0.025 | 3.13 |
| Target B RSV A 100% Fluorescent | RAP2-1 | 95.9 | 0.025 | 2.61 |
| Target C RSV B 100% Fluorescent | RBP1-1 | 101.1 | 0.025 | 2.47 |
|  | Promega V6231, TE | n/a | n/a | 391.79 |
|  | Total |  |  | 400.00 |

TABLE 10

25X Primer Mix

| Primer set | Name | Stock Conc, μM | Conc of 1x, μM | Vol, μL |
|---|---|---|---|---|
| Target A set | RHF1 | 97.7 | 0.1 | 10.24 |
|  | RHR1 | 96.7 | 0.1 | 10.34 |
| Target B set | RAF2 | 102.2 | 0.1 | 9.78 |
|  | RAR2 | 94.7 | 0.1 | 10.56 |
| Target C set | RBF1 | 94.2 | 0.1 | 10.62 |
|  | RBR1 | 94.7 | 0.1 | 10.56 |
|  | Promega V6231, TE | n/a | n/a | 337.90 |
|  | Total |  |  | 400.00 |

TABLE 11

Reaction Master Mix

| Name | 1 rxn | 24 rxns |
|---|---|---|
| 4x TaqPath with MP | 5 μL | 120 |
| 25X Primer mix | 0.8 | 19.2 |
| 25X Fluorescent probe oligo mix | 0.8 | 19.2 |
| water | 8.4 | 201.6 |

TABLE 12

Templates

| Target | Name | Conc |
|---|---|---|
| Target A | RHT1 | 2E3 copies/μL |

TABLE 12-continued

Templates

| Target | Name | Conc |
|---|---|---|
| Target B | RAT2 | 2E3 copies/μL |
| Target C | RBT1 | 2E3 copies/μL |
| No template control | NTC TE | NA |

TABLE 13

Cycling parameters

| Step | time(seconds) | temperature(° C.) | |
|---|---|---|---|
| 1 | 120 | 25 | |
| 2 | 600 | 53 | |
| 3 | 120 | 95 | |
| 4 | 3 | 95 | |
| 5 | 30 | 60 | detection |
| repeat step 4 & 5 90 cycles | | | |

The qPCR protocol for each of the 10 master mixes were tested with known single-stranded DNA templates at DNA templates with a fixed concentration of 10,000 copies per reaction (Table 12). The qPCR reactions were performed on a standard qPCR instrument with the parameters displayed in Table 13. The results from this experiment are displayed in Table 14 and in FIG. 4A. Six replicates were performed along with a no template control (NTC).

TABLE 14

Data from RT-qPCR with no competitive probes

| Target | Replicate 1 | Replicate 2 | Replicate 3 | Replicate 4 | Replicate 5 | Replicate 6 | NTC |
|---|---|---|---|---|---|---|---|
| Target A | 0.4016 | 0.4028 | 0.3967 | 0.4018 | 0.4057 | 0.4056 | 0.0631 |
| Target B | 0.5291 | 0.5235 | 0.4415 | 0.5147 | 0.5324 | 0.5331 | NA |
| Target C | 0.4535 | 0.4415 | 0.4449 | 0.4445 | 0.4438 | 0.4381 | 0.0600 |

TABLE 15

Fluorescence score for experiment without competitive probes

| Target | Name | Score |
|---|---|---|
| Target A | RH T1 | 0.4023 |
| Target B | RSV A T2 | 0.5263 |
| Target C | RSV B T1 | 0.4441 |

To calculate the desired ratio of fluorogenic probe to completive probe for a leveled mix, the median fluorescence level from the 6 replicates was determined from the data from the fluorescent probe only experiment (Table 15). Target C was set to the highest intensity level and left at 100% of the initial concentration of fluorogenic probe. The levels for Target A and Target B were engineered to be distinct by replacing a proportion of the fluorescent probe with a non-fluorescent, competitive probe. The total amount of probe (fluorescent plus non-fluorescent, competitive) was the same for every target and identical to the total probe concentrations for the experiments shown in FIG. 4A.

Table 16 displays the composition of the oligo master mix, which contained the indicated fluorescent probes and competitive probes. The primer master mix and reaction master mix used was the same as those displayed in Table 10 and Table 11 respectively. The templates and cycling parameters used were the same as those displayed in Tables 12 and Table 13 respectively.

Six replicates along with a no template control (NTC) were performed. The resulting data is displayed in Table 17 and FIG. 4B. The fluorescence score calculated for each target is displayed in Table 18.

TABLE 16

Fluorescent and Competitive probe oligo mix

| Probe | Name | Stock Conc, µM | Conc of 1X, µM | Vol, µL |
|---|---|---|---|---|
| Target A-Fluorescent | RHP1-1 | 53.7 | 0.0125 | 4.67 |
| Target A-Competitive | RHP1-0 | 90.2 | 0.0125 | 2.76 |
| Target B-Fluorescent | RAP2-1 | 9.59 | 0.0044 | 9.11 |
| Target B-Competitive | RAP2-0 | 93.8 | 0.0206 | 4.40 |
| Target C-Fluorescent | RBP1-1 | 101.1 | 0.0250 | 4.95 |
| | Promega V6231, TE | n/a | n/a | 774.11 |
| | Total | | | 800.00 |

TABLE 17

Data from RT-qPCR with competitive probes

| Target | Replicate 1 | Replicate 2 | Replicate 3 | Replicate 4 | Replicate 5 | Replicate 6 | NTC |
|---|---|---|---|---|---|---|---|
| Target A | 0.2154 | 0.2121 | 0.2072 | 0.2129 | 0.2142 | 0.2161 | 0.0369 |
| Target B | 0.1192 | 0.1174 | 0.1145 | 0.1169 | 0.1129 | 0.1214 | 0.0359 |
| Target C | 0.4323 | 0.4247 | 0.4195 | 0.4190 | 0.4217 | 0.4243 | 0.0374 |

TABLE 18

Fluorescence score for experiment with competitive probes

| Target | Name | Score |
|---|---|---|
| Target A | RH T1 | 0.2135 |
| Target B | RSV A T2 | 0.1171 |
| Target C | RSV B T1 | 0.4230 |

Example 5

An ELISA assay is performed to detect three proteins of interest within a single reaction vessel. The sets of primary antibodies are adhered to a surface of a reaction vessel. One of each sets is able to uniquely bind to one of each of the three proteins of interest. A sample comprising the three proteins of interest is added to the reaction vessel and each favorably binds to the corresponding primary antibody. A wash procedure is performed to removed unbound sample. Next, three sets of secondary antibodies are added to the reaction vessel, one of the sets corresponding to each of the three proteins of interest.

Set 1 comprises 25% unlabeled competitive secondary antibodies and 75% labeled secondary antibodies, which are labeled with a green fluorophore. The secondary antibodies in Set 1 are identical other than the presence of the fluorescent label.

Set 2 comprises 50% unlabeled competitive secondary antibodies and 50% labeled secondary antibodies, which are labeled with a green fluorophore. The secondary antibodies in Set 2 are identical other than the presence of the fluorescent label. The green fluorophore used in Set 2 is the same green fluorophore used in Set 1.

Set 3 comprises 75% unlabeled competitive secondary antibodies and 25% labeled secondary antibodies, which are labeled with a green fluorophore. The secondary antibodies in Set 3 are identical other than the presence of the fluorescent label. The green fluorophore used in Set 3 is the same green fluorophore used in Set 1 and Set 2.

The secondary antibodies within each of Sets 1-3 are distinct from each other since they are selected for their ability to specifically bind to their corresponding protein of interest. However, the fluorophore used to label the labeled secondary antibodies within each set is the same. Also, the ratio of unlabeled to labeled secondary antibodies within each set are different and unique compared to the other sets.

The three sets of secondary antibodies are added to the reaction vessel. Labeled and unlabeled secondary antibodies from each set compete for binding to their corresponding protein epitope. Because the labeled and unlabeled secondary antibodies within each set are identical other than the presence of the fluorophore, their binding kinetics are basically the same. After the binding step, a wash procedure is performed to remove unbound secondary antibody.

An excitation source excites the green fluorophores and a signal is emitted from each of the bound labeled secondary antibodies. Three distinct signal intensities are detected and measured. Each signal intensity correlated to a specific ratio. Because each set of secondary antibodies comprised a unique ratio of labeled to unlabeled secondary antibodies, a unique signal intensity can be correlated to that specific set of secondary antibodies. Therefore, each unique signal intensity is used to identify one of each of the three proteins of interest.

Example 6 mRNA is isolated from a sample following an experiment and processed for sequencing. The mRNA sample reverse transcribed to cDNA and then PCR amplified in order to prepare the sequencing library. Sequencing is performed to detect a target of interest and to determine how the target level has changed due to the conditions of the experiment compared to a control gene. Unfortunately, the target is from a very highly expressed gene and is over-represented in the sequencing library compared to the control gene. This makes it difficult to accurately calculate the impact of the experimental conditions on the expression level of the gene.

The frustrated scientists go back to the original cDNA sample and re-amplify it by PCR. However, this time, they include a different set of target specific primers in the PCR reaction mix. The set of target primers comprises 25% functional primers capable of being extended during PCR, and 75% of competitive primers which cannot be extended due to a capped end.

The resulting sequencing results has a lower level of the first transcript, which allows for a more accurate calculation of the transcription level caused by the conditions used in the original experiment.

What is claimed is:

1. A method of identifying a first target nucleic acid in a sample comprising:
    providing a sample comprising the first target nucleic acid;
    adding a first set of paired oligonucleotide probes comprising a sequence complementary to a common region of the first target nucleic acid to the sample;
    amplifying the first target nucleic acid with a polymerase chain reaction using a polymerase having 5' to 3' exonuclease activity in the presence of the first set of paired oligonucleotide probes and primers specific for the first target nucleic acid, wherein the first set of paired oligonucleotide probes comprises a first signal oligonucleotide probe and a first competitive oligonucleotide probe, and the first signal oligonucleotide probe and the first competitive oligonucleotide probe compete with one another for binding to the common region of the first target nucleic acid in the sample, the first set of paired oligonucleotide probes comprising a known first ratio of the first signal oligonucleotide probe to the first competitive oligonucleotide probe,
wherein the first signal oligonucleotide probe comprises a first fluorescence signal tag and a signal quenching tag that quenches a fluorescent signal generated from the first fluorescence signal tag prior to the signal quenching tag being separated from the first fluorescence signal tag during the polymerase chain reaction,
wherein the first competitive oligonucleotide probe does not comprise a fluorescence signal tag, and
    wherein the amplifying step causes the first signal oligonucleotide probe bound to the first target nucleic acid to be degraded by the polymerase, the signal quenching tag to be separated from the first fluorescence signal tag on the first signal oligonucleotide probe, and a first fluorescent signal to be generated from the first fluorescence signal tag after the first fluorescence signal tag is separated from the signal quenching tag;
    measuring an intensity of the first fluorescent signal;
    correlating the intensity of the first fluorescent signal to the first ratio; and
    identifying the first target nucleic acid in the sample based on said correlating the intensity of the first fluorescent signal to the first ratio.

2. The method of claim 1, wherein the sample comprises a second target nucleic acid.

3. The method of claim 2, further comprising identifying the second target nucleic acid by:
    adding a second set of paired oligonucleotide probes comprising a sequence complementary to a common region of the second target nucleic acid to the sample;
    amplifying the second target nucleic acid in the same polymerase chain reaction using the polymerase having 5' to 3' exonuclease activity in the presence of the second set of paired oligonucleotide probes and primers specific for the second target nucleic acid, wherein the second set of paired oligonucleotide probes comprises a second signal oligonucleotide probe and a second competitive oligonucleotide probe, and the second signal oligonucleotide probe and the second competitive oligonucleotide probe compete with one another for binding to the common region of the second target nucleic acid in the sample, the second set of paired oligonucleotide probes comprising a known second ratio of the second signal oligonucleotide probe to the second competitive oligonucleotide probe, wherein the second signal oligonucleotide probe comprises a second fluorescence signal tag and a signal quenching tag that quenches a fluorescent signal generated from the second fluorescence signal tag prior to the signal quenching tag being separated from the second fluorescence signal tag during the polymerase chain reaction,
wherein the second competitive oligonucleotide probe does not comprise a fluorescence signal tag, and
    and, wherein the amplifying step causes the second signal oligonucleotide probe bound to the second target nucleic acid to be degraded by the polymerase, the signal quenching tag to be separated from the second fluorescence signal tag on the second signal oligonucleotide probe, and a second fluorescent signal to be generated from the second fluorescence signal tag after the second fluorescence signal tag is separated from the signal quenching tag;
    measuring an intensity of the second fluorescent signal;
    correlating the intensity of the second fluorescent signal to the second ratio; and
    identifying the second target nucleic acid in the sample based on said correlating the intensity of the second fluorescent signal to the second ratio, wherein the first fluorescence signal tag and the second fluorescence signal tag are identical, the first ratio is different from the second ratio, the intensity of the first fluorescent signal is different from the intensity of the second fluorescent signal, and the first target nucleic acid and the second target nucleic acid are identified based on different signal intensities of the first fluorescent signal and the second fluorescent signal.

4. The method of claim 3, wherein the total concentration of the first set of paired oligonucleotide probes is the same as the total concentration of the second set of paired oligonucleotide probes in a mixture formed by the sample, the first set of paired oligonucleotide probes, and the second set of paired oligonucleotide probes before the polymerase chain reaction.

5. The method of claim 3, wherein the second ratio is selected from the group consisting of about 1:1, about 1:2, about 1:3, about 1:4, about 1:5, about 1:6, about 1:7, about 1:8, about 1:9, about 1:10, about 1:16, and about 1:20.

6. The method of claim 1, wherein the first set of paired oligonucleotide probes comprise quantitative polymerase chain reaction (qPCR) probes.

7. The method of claim 1, wherein the first fluorescent signal is generated by exciting the first fluorescence signal tag.

8. The method of claim 1, wherein the first competitive oligonucleotide probe and the first signal oligonucleotide probe comprise at least one modified end.

9. The method of claim 8, wherein the modified end prevents enzymatic extension of the modified end by the polymerase during the process of the polymerase chain reaction.

10. The method of claim 1, wherein the first ratio is selected from the group consisting of about 1:1, about 1:2, about 1:3, about 1:4, about 1:5, about 1:6, about 1:7, about 1:8, about 1:9, about 1:10, about 1:16, and about 1:20.

11. The method of claim 1, wherein the first competitive oligonucleotide probe is a molecular beacon competitive oligonucleotide probe and the first signal oligonucleotide probe is a molecular beacon signal oligonucleotide probe.

* * * * *